United States Patent
Licht

(10) Patent No.: US 10,716,857 B2
(45) Date of Patent: Jul. 21, 2020

(54) COMPOSITION FOR TREATMENT OF WARTS

(75) Inventor: Flemming Licht, Vanlose (DK)

(73) Assignee: ABBEX AB, Solna (SE)

( * ) Notice: Subject to any disclaimer, the term of this patent is extended or adjusted under 35 U.S.C. 154(b) by 0 days.

(21) Appl. No.: 14/403,007

(22) PCT Filed: May 28, 2012

(86) PCT No.: PCT/SE2012/050566
§ 371 (c)(1),
(2), (4) Date: Dec. 22, 2014

(87) PCT Pub. No.: WO2013/180606
PCT Pub. Date: Dec. 5, 2013

(65) Prior Publication Data
US 2015/0165031 A1   Jun. 18, 2015

(51) Int. Cl.
| | |
|---|---|
| *A61K 47/14* | (2017.01) |
| *A61K 31/19* | (2006.01) |
| *A61K 9/00* | (2006.01) |
| *A61K 9/08* | (2006.01) |
| *A61K 31/22* | (2006.01) |
| *A61K 31/194* | (2006.01) |

(52) U.S. Cl.
CPC ............ *A61K 47/14* (2013.01); *A61K 9/0014* (2013.01); *A61K 9/08* (2013.01); *A61K 31/19* (2013.01); *A61K 31/194* (2013.01); *A61K 31/22* (2013.01)

(58) Field of Classification Search
CPC .... A61K 2300/00; A61K 31/19; A61K 31/22; A61K 31/194; A61K 47/14; A61K 9/0014; A61K 9/08
See application file for complete search history.

(56) References Cited

U.S. PATENT DOCUMENTS

| | | | |
|---|---|---|---|
| 5,476,664 A | 12/1995 | Robinson et al. | |
| 5,525,358 A | 6/1996 | Popp | |
| 6,503,946 B1 * | 1/2003 | Agholme | A61K 31/19 |
| | | | 514/557 |
| 2004/0109899 A1 | 6/2004 | Albahri | |
| 2006/0110415 A1 * | 5/2006 | Gupta | A61K 8/0212 |
| | | | 424/401 |
| 2008/0153757 A1 | 6/2008 | Beeson et al. | |
| 2010/0113593 A1 | 5/2010 | Meyer | |
| 2010/0119584 A1 | 5/2010 | Matsuzawa et al. | |

FOREIGN PATENT DOCUMENTS

| | | | |
|---|---|---|---|
| CN | 86107485 A * | 5/1988 | |
| CN | 1939539 A | 4/2007 | |
| EP | 1143966 A1 | 10/2001 | |
| EP | 2460509 A1 | 6/2012 | |
| WO | WO-0045808 A1 | 8/2000 | |
| WO | WO-2008128627 A2 | 10/2008 | |
| WO | WO-2011028110 A1 * | 3/2011 | ............. A61K 8/368 |

OTHER PUBLICATIONS

Human Papilloma Viruses (Dr. Reddy's Pediatric Office on the Web, last revised Jun. 16, 2010).*
Chinese Office Action dated Jan. 4, 2016 issued in corresponding Chinese Application No. 201280073392.3 (with English translation).
Eurasian Patent Organization Office Action dated Jan. 14, 2016 issued in corresponding Eurasian Patent Organization Application No. 201491927/28 (with English translation).
New Zealand Office Action dated Feb. 2, 2016 issued in corresponding New Zealand Application No. 702424.
Hanzhang Qin et al., "Chinese Wine Dictionary", Hongqi Press, First Edition, Apr. 1998, pp. 974-983.
European Office Action dated Feb. 29, 2012, issued in corresponding European Application No. 11191792.8.
Japanese Office Action dated Aug. 25, 2015 issued in corresponding Japanese Application No. 2015-513968 (with English translation).
Ukranian Office Action dated Aug. 27, 2015 issued in corresponding Ukranian Application No. 17879/3A/15 (no English translation).
Kaitei Iyakuhinn Tennkabutu Handbook (English title: Handbook of Pharmaceutical Excipients). Yakuji Nippo Limited, Feb. 28, 2007, p. 645-647.
Shamsadini S et al., "Topical formic acid for the treatment of common warts", The Gulf Journal of Dermatology, vol. 11, No. 2, Oct. 2004, pp. 33-35.
Bhat R M et al., "Topical formic acid puncture technique for the treatment of common warts", Interntaional journal of dermatology, Wiley-Blackwell publishing Ltd, UK, vol. 40, No. 6, Jun. 1, 2001, pp. 415-419.
Abbott L G, "Warts", Bulletin of the Post-Graduate Committee in Medicine, University of Sydney, vol. 19, Mar. 1, 1964, pp. 301-304.
International Search Report PCT/ISA/210 for International Application No. PCT/SE2012/050566 dated Feb. 12, 2013.
Shamsadini S et al., "Treatment of warts with topical formic acid[1]", Iranian Journal of Medical Sciences, Shiraz University Publications, Shiraz, Iran, vol. 30, No. 4, Jan. 2005, p. 199.
European Office Action dated Nov. 19, 2014 issued in corresponding European Application No. 11191792.8.
Chen "A" Chinese non-patent literature and English translation "How to choose a better Eyeliner", which is an excerpt from Wan Shi Bu Qui Ren, published by New World Press, pp. 54, (2011) (partial English translation provided).

* cited by examiner

*Primary Examiner* — Jean P Cornet

(57) ABSTRACT

The present invention concerns a pharmaceutical composition comprising formic acid and at least one C1-C4 alkyl ester of lactic acid, malic acid, tartaric acid, citric acid, preferably ethyl lactate, for the topical treatment of warts.

12 Claims, No Drawings

COMPOSITION FOR TREATMENT OF WARTS

CROSS-REFERENCE TO RELATED APPLICATIONS

This application is a national phase under 35 U.S.C. § 371 of PCT International Application No. PCT/SE2012/050566 which has an International filing date of May 28, 2012.

The present invention relates to a composition for the treatment of warts. In particular, it concerns a composition for the topical treatment of warts in mammals, such as humans.

TECHNICAL BACKGROUND

The European patent 1143966 B1 describes the use of a preparation comprising formic acid as an active ingredient for the manufacture of a medicament for the treatment of warts caused by virus in a mammal, by topical administration of the medicament on the affected area. The patent teaches that the wart should be softened with hot water and that, if necessary, hard skin covering the wart should be scraped of, before treatment with formic acid.

Bhat et al. ("Topical formic acid puncture technique for the treatment of common warts", International Journal of Dermatology 2001, 40, 415-419) discloses a topical application/needle puncture technique for the treatment of warts.

SUMMARY OF THE INVENTION

The needle puncture technique has been regarded as the best wart treatment using formic acid, as the puncture technique has hitherto provided the best reproducible results.

There is a continued need for alternative means for the treatment of warts. Several demands may be put on such means. It may preferably be inexpensive, easy to manufacture, storage stable, effective, and should work shortly after application, allowing warts to be eradicated within a short time span. In addition, it should preferably be easy to apply without the aid from medical expertise, non-toxic, and not be associated with discomfort for the patient, i.e. it should not have a repulsive smell or be painful for the patient during or after administration.

Some patients complain that acid based means for the topical treatment of warts have low efficacy, take several weeks to act, are foul-smelling and may be painful to apply.

There is a need for a composition which a patient may apply without the need of any preparatory steps, before application of the composition on the warts.

It has surprisingly been identified that a composition comprising formic acid and at least one C1-C4 alkyl ester of lactic acid, malic acid, tartaric acid, or citric acid, preferably ethyl lactate, has particular advantages for the topical treatment of warts.

In particular, it has surprisingly been identified that the inclusion in the composition of at least one C1-C4 alkyl ester of lactic acid, malic acid, tartaric acid, or citric acid, preferably ethyl lactate, provides the same effect as using the puncture technique for improving the effect of the acid on the warts.

It has been identified that it may not be necessary to remove hard skin covering warts by use of a composition according to the present invention.

Further, it has surprisingly been identified that the high concentrations proposed by the prior art may not be necessary in all cases, by using a composition according to the present invention.

Experiments indicate that the inclusion in the composition of at least one C1-C4 alkyl ester of lactic acid, malic acid, tartaric acid, or citric acid, preferably ethyl lactate, reduces the contact angle of the composition, i.e. reduces the surface tension. Without being bound by any theory, it may be speculated that the number or strengths of hydrogen bonds in the composition is decreased by the inclusion of one of the alkyl esters, such as ethyl lactate, thereby decreasing the contact angle. Inclusion of water and/or alcohol may increase the contact angle. Decreased contact angle makes it easier for the composition to adhere to warts, and following to be absorbed by warts, i.e. improving the penetration of the composition of the invention. Improved penetration may further emphasize any antiviral effects of formic acid. Additionally, reduced surface tension makes it easier to apply the composition in the adequate amount, with reduced risk of inadvertently smearing composition on adjacent, healthy skin. The reduced surface tension may easily be tested by placing a drop of the composition of the invention on a plate, and comparing with a drop of a composition of the prior art, such as a composition comprising water and formic acid.

It has been realized by the inventor that it may be beneficial to distinguish between soft warts and hard warts.

In particular, it has been identified that a composition with a lower content of acid may be preferable in the treatment of soft warts, as a composition with higher content of acid is more likely to give damages upon accidental application on the surrounding skin. Further, it has been discovered that the use of a composition with high content of acid on soft warts gave unwanted side effects in some cases. However, higher content of acids are particularly suitable for hard wards, which are difficult to remove.

The exact mechanism of action of formic acid in relation to the treatment of warts is not known. Dehydration with subsequent destruction of wart infected tissue has been proposed. In addition, formic acid may prevent virus particles from attaching to healthy cells, thereby inhibiting viral transmission.

It may be speculated that there is a synergistic effect between formic acid and at least one C1-C4 alkyl ester of lactic acid, malic acid, tartaric acid, or citric acid, such as ethyl lactate, providing a strong effect against warts. Without being bound by any theory, the inventor of the present invention speculate that formic acid in itself acts as an active ingredient, while e.g. ethyl lactate acts as an active carrier, allowing the concentration of acid to be kept locally sufficiently low to impede irritation for the patient. It is additionally speculated that such a carrier allow the acid to penetrate deeper into the warts. Further, the inventor speculates that formic acid and ethyl lactate in the presence of water may react to form lactic acid, which independently acts as an active ingredient.

Aspects and embodiments of the present invention are provided here. It will be clear for the person skilled in the art that these may be combined.

According to an aspect, the invention provides the use of formic acid and at least one C1-C4 alkyl ester of lactic acid, malic acid, tartaric acid, or citric acid, preferably ethyl lactate, for the manufacture of a composition for the topical treatment of warts.

According to an aspect, the invention concerns the use of a composition comprising formic acid and at least one C1-C4 alkyl ester of lactic acid, malic acid, tartaric acid, or citric acid, preferably ethyl lactate, for the topical treatment of warts.

According to an aspect, the invention concerns a pharmaceutical composition comprising formic acid and at least one C1-C4 alkyl ester of lactic acid, malic acid, tartaric acid, or citric acid, preferably ethyl lactate, for the treatment of warts.

According to an aspect, the invention concerns a pharmaceutical composition for the topical treatment of warts, comprising formic acid and being free of water and/or alcohol.

According to an aspect, the invention concerns a method of treating warts, comprising topically administering a composition comprising formic acid and at least one C1-C4 alkyl ester of lactic acid, malic acid, tartaric acid, or citric acid, preferably ethyl lactate, to a patient in need thereof.

According to yet an aspect, the invention concerns a pen, comprising a composition according to the invention, for topical administration of a composition according to the invention. A pen has shown to be particularly useful for the application of a pharmaceutical composition according to the invention, as exact control of the precise location of application of the composition may be achieved by the topical application on a wart with the pen. Further, the composition may be rubbed or massaged into a wart with the tip of the pen.

DETAILED DISCLOSURE

The invention concerns a composition comprising formic acid and at least one C1-C4 alkyl ester of lactic acid, malic acid, tartaric acid, or citric acid, preferably ethyl lactate. Such a composition may be used for the treatment of warts, typically by topical treatment of warts.

According to an aspect, there is provided a composition comprising formic acid and at least one C1-C4 alkyl ester of lactic acid, malic acid, tartaric acid, citric acid, or a mixture of any of these, for use in topical treatment of warts.

Such a composition may be applied with a soft cotton pad or cotton stick swab, or a pen, i.e. without scraping skin of the warts and without the need of puncturing the warts before application. Scraping skin of the warts and/or puncturing the warts may be associated with pain and should thus be avoided. Avoiding scraping and/or puncturing may improve patient compliance.

In one embodiment of this aspect, said at least one C1-C4 alkyl ester is ethyl lactate.

Ethyl lactate, also known as lactic acid ethyl ester, is found naturally, and carries a pleasant odor. Ethyl lactate may be produced from biological sources, e.g. by fermentation. Ethyl lactate may be either the levo (S) or dextro (R) form or a mixture of the two. Industrially produced ethyl lactate may consist of a racemic mixture of levo and dextro forms.

According to an embodiment, ethyl lactate used in the present invention is a racemic mixture.

According to another embodiment, ethyl lactate used in the present invention is ethyl (−)-L-lactate, or more than 50% of the ethyl lactate is ethyl (−)-L-lactate. This may be obtained by using ethyl lactate derived from natural sources. According to a preferred embodiment ethyl lactate is ethyl-S(−)-2-hydroxy propanoate. Preferably it is obtained by fermentation from sugar.

Compositions according to the present invention preferably comprise ethyl lactate. According to an embodiment it is contemplated that this ingredient may be partly or fully substituted with at least one C1-C4 alkyl ester of lactic acid, malic acid, tartaric acid, citric acid, or a mixture of any of these. The inventor of the present invention speculates that these alkyl esters may have anti-viral effect and/or suitable transport enhancing properties. Among the C1-C4 of relevance for the present invention may be mentioned methyl, ethyl, n-propyl, isopropyl, n-butyl, sec-butyl, isobutyl and tert-butyl esters. If suitable, any or all carboxy groups may be esterified. Monoalkyl, dialkyl and/or trialkyl esters may be suitable. Preferred esters are ethyl esters, further preferred are isopropyl esters. In addition to ethyl lactate, further preferred compounds are diethyl malate, diisopropyl malate, monoethyl tartrate, diethyl tartrate, monoethyl citrate and triethyl citrate.

According to an embodiment it is further contemplated that ethyl lactate may be partly or fully substituted with other ingredients with similar properties, such as lactic acid, preferably L-lactate, malic acid, tartaric acid, citric acid, acetic acid, glycolic acid, propionic acid, 3-hydroxypropanoic acid, malonic acid, butyric acid, hydroxybutyric acid, 1-propanol, 2-propanol, propionaldehyde, acrolein or sodium lactate, or a mixture of any of these.

A range of types of warts has been identified, varying in shape and site affected, as well as the type of human papilloma virus involved. These include, but are not limited to: common wart (*Verruca vulgaris*), flat wart (*Verruca plana*), filiform or digitate wart, plantar wart (*Verruca Pedis*), mosaic wart, genital wart (veneral wart, *Condyloma acuminatum, Verruca acuminate*), and periungal wart.

According to an embodiment, the invention concerns the use of a composition according to the invention, wherein the warts are selected among the group consisting of common wart (*Verruca vulgaris*), flat wart (*Verruca plana*), filiform or digitate wart, plantar wart (*Verruca Pedis*), mosaic wart, genital wart (veneral wart, *Condyloma acuminatum, Verruca acuminate*), and periungal wart.

According to an embodiment, the invention concerns the use of a composition of the invention, wherein the warts are common warts.

According to an embodiment, the invention concerns the use of a composition of the invention, wherein the warts are plantar or flat warts.

According to an embodiment, the invention concerns the use of a composition of the invention, wherein the warts are filiform or digitate warts.

According to an embodiment, the invention concerns the use of a composition of the invention, wherein the warts are caused by human papillomavirus (HPV), such as a genotype of HPV causing warts selected among the group consisting of *verruca vulgaris, verruca plantaris, verruca plana*, and *condyloma acuminatum*.

According to an embodiment, the invention concerns the use of a composition of the invention, wherein the warts are caused by human papillomavirus (HPV), such as a type of HPV selected among the group consisting of the types 1, 2, 3, 4, 5, 6, 7, 8, 9, 10, 11, 12, 13, 14, 16, 18, 26, 27, 28, 29, 31, 32, 33, 35, 39, 40, 42, 43, 44, 45, 49, 51, 52, 53, 54, 56, 57, 58, 59, 61, 63, 66, 68, 72, 73, 81, 82, and 89.

According to an embodiment, the invention concerns a composition for application directly on the warts without puncturing the warts or scraping skin of the warts.

According to an embodiment, the invention concerns a composition for application with a soft pen or cotton pad.

According to an embodiment, the invention concerns a composition, wherein the total amount (w/w) of formic acid in the composition is 1-95%, preferably 2-90%, more preferred 3-85%, preferably 5-80%, more preferred 10-70%, preferably 15-65%, more preferably 20-60%, more preferred 25-50%, preferably 30-40%, more preferred 30-35%.

According to an embodiment the invention concerns a composition, wherein the total amount (w/w) of formic acid in the composition is 60-95%, more preferred 70-90%, preferably 80-85%. Such a composition is particularly preferred for use on hard warts. Weekly application is particularly preferred for such a composition.

According to an embodiment the invention concerns a composition for use, wherein the total amount (w/w) of formic acid in the composition is 60-95%, more preferred 70-90%, preferably 80-85%.

According to an embodiment the invention concerns a composition for use, wherein said composition comprises 80-85% formic acid (w/w); 15-20% ethyl lactate (w/w); and substantially no water and/or alcohol.

According to an embodiment the invention concerns such a composition, for wherein said composition is for use on hard warts.

According to an embodiment the invention concerns such a composition, for use on the palm or the foot sole.

According to an embodiment the invention concerns such a composition, wherein the warts are selected among the group consisting of common wart (*Verruca vulgaris*), plantar wart (*Verruca pedis*), and mosaic wart.

Alternatively, according to an embodiment the invention concerns a composition, wherein the total amount (w/w) of formic acid in the composition is 10-60%, more preferred 15-50%, preferably 20-40%, more preferred 30-35%. Lower percentage of formic acid improves the smell of the composition and tends to increase patient compliance. This composition is particularly preferred for use on soft warts. Daily application is particularly preferred for this composition.

According to an embodiment the invention there is provided a composition for use, wherein said composition comprises 30-35% formic acid (w/w); 65-70% ethyl lactate (w/w); and substantially no water and/or alcohol. This composition is particularly useful for use on soft warts.

According to an embodiment the invention concerns this composition, for use on other sites than the palm or the foot sole.

According to an embodiment the invention concerns this composition for use on the back of the foot, the back of the hand, the face, neck, wrists, knees or genitalia.

According to an embodiment the invention concerns this composition, wherein the warts are selected among the group consisting of flat wart (*Verruca plana*), filiform or digitate wart, genital wart (veneral wart, *Condyloma acuminatum, Verruca acuminate*), and periungal wart.

According to an embodiment, the invention concerns a composition, wherein the total amount (w/w) of alkyl ester, such as ethyl lactate, in the composition is 1-95%, preferably 2-90%, more preferred 3-85%, preferably 5-80%, more preferred 10-70%, preferably 15-65%, more preferably 20-60%, more preferred 25-50%, preferably 30-40%, more preferred 30-35%.

According to an embodiment, the invention concerns a composition, wherein the total amount (w/w) of said C1-C4 alkyl ester, such as ethyl lactate, in the composition is 40-90%, more preferred 50-85%, preferably 60-80%, more preferred 65-70%.

According to an embodiment, the invention concerns a composition, wherein the total amount (w/w) of said C1-C4 alkyl ester, such as ethyl lactate, in the composition is 2-50%, more preferred 3-40%, preferably 5-35%, more preferred 10-30%, preferably 15-20%.

According to an embodiment, the invention concerns a composition, wherein the composition comprises lactic acid, preferably wherein the total amount (w/w) of lactic acid in the composition is 2-90%, more preferred 3-85%, preferably 5-80%, more preferred 10-70%, preferably 15-65%, more preferably 20-60%, more preferred 30-50%, preferably 35-40%.

According to an embodiment, the invention concerns a composition, wherein the total combined amount of formic acid and C1-C4 alkyl ester, such as ethyl lactate, in the composition is at least 60%, more preferred at least 70%, preferably at least 80%, more preferred at least 90%, preferably at least 95%, more preferably at least 97%, more preferred at least 98%, preferably at least 99%, more preferred 100% (w/w).

According to a further embodiment of the present invention, pharmaceutically acceptable carriers, such as water, oil, glycerol, alcohol or mixtures thereof, can be included in a composition according to the invention, e.g. to achieve a further softening effect on and around the warts.

According to an embodiment, a composition according to the invention may comprise additional active ingredients or excipients. Examples comprise, but are not limited to, *Callitris Intratropica, Lavandula Angustifolia, Melaleuca Alternifolia*, lemon oil, and mixtures of any of these. The person skilled in the art is familiar with additional pharmaceutically acceptable excipients which may be combined with the present invention.

According to an embodiment, a composition according to the invention may be made substantially free of water and/or ethanol.

According to an embodiment, the invention concerns a composition for the topical treatment of warts comprising formic acid as an active ingredient, and less than 15%, preferably less than 10%, more preferred less than 5%, preferably less than 3%, more preferred substantially no water and/or alcohol such as ethanol.

According to an embodiment, the invention concerns a composition for the topical treatment of warts comprising formic acid as an active ingredient, such as a composition according to the invention, and further comprising at least one colorant, e.g. a dye or a pigment, such as carotene. This embodiment may facilitate correct application on warts, and avoid application on surrounding tissue and skin. Particularly preferred is a colorant with a discrete color, or a color, which vanishes from the warts after application. This may improve patient compliance.

According to an embodiment, a composition according to the invention may be in the form of an emulsion, cream, paste, ointment, lotion, suspension, gel, spray, and/or together with topical carriers suitable for the treatment.

According to an embodiment, a composition according to the invention may be for human use or for veterinary use.

According to an embodiment, the invention concerns a pharmaceutical composition for medical use.

According to an embodiment, the invention concerns a pharmaceutical composition comprising formic acid and at least one C1-C4 alkyl ester of lactic acid, malic acid, tartaric acid, citric acid, or a mixture of any of these, preferably ethyl lactate; preferably for the treatment of warts.

According to an embodiment, the invention concerns use of formic acid and at least one C1-C4 alkyl ester of lactic acid, malic acid, tartaric acid, citric acid, or a mixture of any of these, for the manufacture of a composition according to the invention, such as for the topical treatment of warts.

In another aspect of the invention there is provided a method of treating warts, comprising topically administering a composition comprising formic acid and at least one C1-C4 alkyl ester of lactic acid, malic acid, tartaric acid, citric acid, or a mixture of any of these, to a patient in need thereof.

In one embodiment of this aspect, said at least one C1-C4 alkyl ester is ethyl lactate.

In another embodiment of this aspect, said composition is applied directly on the warts without puncturing the warts or scraping skin of the warts.

In another embodiment of this aspect, the total amount (w/w) of formic acid in the composition is 60-95%, more preferred 70-90%, preferably 80-85%.

In another embodiment of this aspect, the composition comprises 80-85%; of formic acid (w/w); 15-20% ethyl lactate (w/w); and substantially no water and/or alcohol. Said composition may be applied on hard warts. Typically, said composition is applied on the palm or the foot sole.

In another embodiment of this aspect, the total amount (w/w) of formic acid in the composition is 10-60%, more preferred 15-50%, preferably 20-40%, more preferred 30-35%.

In an alternative embodiment of this aspect, the composition comprises 30-35% (w/w) of formic acid; 65-70% (w/w) of ethyl lactate; and substantially no water and/or alcohol. Said composition may be applied on soft warts. Said composition may be applied on other sites than the palm or the foot sole, such as on the back of the foot, the back of the hand, the face, neck, wrists, knees or genitalia. In these compositions, there may be less than 15%, preferably less than 10%, more preferred less than 5%, preferably less than 3%, more preferred substantially no water and/or alcohol such as ethanol.

In another aspect of the invention, there is provided a composition comprising 30-35% formic acid (w/w); 65-70% ethyl lactate (w/w); and substantially no water and/or alcohol.

In another aspect of the invention, there is provided a composition comprising 80-85% formic acid (w/w); 15-20% ethyl lactate (w/w); and substantially no water and/or alcohol.

All proportions and percentages are in weight/weight unless otherwise mentioned.

All cited references are incorporated by reference.

The accompanying Examples are provided to explain rather than limit the present invention. It will be clear to the person skilled in the art that aspects, embodiments and claims of the present invention may be combined.

EXAMPLES

Example 1

Three different compositions were compared by topical application on warts on human subjects.

A first composition (A) was prepared by mixing 30% formic acid with 70% ethyl lactate (w/w).

A second composition (B) was prepared by mixing 85% formic acid with 15% ethyl lactate (w/w).

The third composition (C) was GSK Duofilm, indicated to comprise 16.7% salicylic acid and 16.7% lactic acid.

90 patients with warts were divided into three groups of 30 patients. The groups received treatment as follows:

Group I: Composition (A). The composition was applied once daily for a maximum of 12 weeks or until the warts were removed.

Group II: Composition (B). The composition was applied once weekly for a maximum of 12 weeks or until the warts were removed.

Group III: Composition (C). The composition was applied once daily for a maximum of 12 weeks or until the warts were removed.

|  | Group I | Group II | Group III |
| --- | --- | --- | --- |
| Number of patients |  |  |  |
| Dropped out | 6 | 7 | 8 |
| Decreased | 3 | 1 | 2 |
| Failure | 3 | 2 | 5 |
| Resolved | 18 | 20 | 15 |
| Sum Patients | 30 | 30 | 30 |
| Dropped out | 20% | 23% | 27% |
| Among non-dropped out patients |  |  |  |
| Decreased | 13% | 4% | 9% |
| Failure | 13% | 9% | 23% |
| Resolved | 75% | 87% | 68% |
| Number of warts |  |  |  |
| Resolution | 50% | 90% | 45% |

"Dropped out" refers to the patients, who did not complete the study, i.e. failed to show up until completion of the study.

In general, higher formic acid concentration led to higher efficacy. However, complaints were also increasing due to pain upon application of the compositions with higher formic acid contents. It was found that composition (A) was especially suitable for treating warts on other places than the feet and hands, such as other places than the palm and the foot sole, while composition (B) was especially suitable for treating warts on feet and hands, particularly on the palm and the foot sole. Of the three tested compositions, composition (C) led to the highest drop-out rate, the highest failure rate among the patients, and the lowest percentage of resolved warts.

Comparison Example 1

A mixture comprising 85% formic acid and 15% water was applied on warts, using a puncture technique.

The results using this puncture technique was comparable to the effect obtained by using the second mixture (B) according to the invention.

However, the use of the second mixture (B) did not necessitate the use of a puncture technique, as the second composition (B) was applied directly on the warts.

Comparison Example 2

A mixture comprising 85% formic acid and 15% water was applied on the skin of a human male. The mixture was foul smelling and painful upon application.

Contemplated Compositions of the Invention

The compositions of Table 1 have been made or are contemplated. The compositions may be manufactured by mixing the ingredients at room temperature.

The compositions may be applied on a wart as a drop, with a cotton stick or with a pen comprising the composition.

TABLE 1

| Composition No. | Formic acid | Ethyl lactate | Lactic acid | Lavender Oil | Callitris intratropica oil | Melaleuca alternifolia oil | Aqua | Glycerol | Total |
|---|---|---|---|---|---|---|---|---|---|
| 1 | 85% | 15% | | | | | | | 100% |
| 2 | 33% | 56% | 10% | 1% | | | | | 100% |
| 3 | 3% | 87% | 10% | | | | | | 100% |
| 4 | 10% | 80% | 10% | | | | | | 100% |
| 5 | 50% | 30% | 20% | | | | | | 100% |
| 6 | 50% | 15% | 30% | 1% | 1% | 1% | 1% | 1% | 100% |
| 7 | 20% | 70% | 10% | | | | | | 100% |
| 8 | 40% | 35% | 20% | 4% | | | | 1% | 100% |
| 9 | 35% | 40% | 5% | 10% | 1% | 4% | | 5% | 100% |
| 10 | 60% | 20% | 5% | | | | 10% | 5% | 100% |
| 11 | 20% | 30% | 10% | 15% | | | 10% | 15% | 100% |
| 12 | 80% | 15% | | 3% | | | | 2% | 100% |
| 13 | 75% | 5% | 15% | | 5% | | | | 100% |
| 14 | 70% | 25% | | 2% | | 2% | | 1% | 100% |
| 15 | 30% | 25% | 40% | | | | | 5% | 100% |
| 16 | 45% | 15% | 40% | | | | | | 100% |
| 17 | 10% | 90% | | | | | | | 100% |
| 18 | 15% | 80% | 5% | | | | | | 100% |
| 19 | 35% | 50% | 10% | | | | 5% | | 100% |
| 20 | 30% | 15% | 50% | 1% | 1% | 1% | 1% | 1% | 100% |
| 21 | 40% | 50% | 10% | | | | | | 100% |
| 22 | 25% | 50% | 25% | | | | | | 100% |
| 23 | 14% | 70% | 10% | 1% | | | | 5% | 100% |
| 24 | 35% | 65% | | | | | | | 100% |
| 25 | 30% | 70% | | | | | | | 100% |

Measurement of Contact Angle

Measurements of the contact angle of mixtures of a) formic acid and water; and b) formic acid and ethyl lactate were conducted according to the following protocol:

1) Coverslip cleaned with methanol were washed with $H_2O$ and dried with $N_2$.

2) The liquid mixtures were mixed on a rotation table for 10 min.

3) Using 2 coverslips for each comparison, three droplets of each of the samples are added onto each of the two coverslips.

Each solution (mixture) was measured on two distinct surfaces (3 drops on each surface). From the contact angle studies a significant difference between the samples was observed. The results are provided in Table 2 below.

TABLE 2

| Average Measured Contact Angles of Mixtures | +water to 100% (w/w) | +ethyl lactate to 100% (w/w) |
|---|---|---|
| 35% formic acid | 31 | 16 |
| 85% formic acid | 18 | 10 |

CONCLUSIONS

Preliminary experiments indicate selected compositions according to the invention may in favorable cases completely eradicate a treated wart within 2-3 days upon daily topical administration. Other cases may require longer time, such as 1, 2 or 3 weeks. Particular success has been achieved with filiform warts in the face of a patient. In contrast, the mixture of the Comparison Example 2 took several weeks, and as an average about a month, before the warts were removed from the hands and feet of the patients. No success with the removal of warts in the face of a patient was reported with the mixture of the Comparison Example.

Further, some subjects have complained about pain upon application of the Comparison Example 2, e.g. if this mixture was applied on skin.

Lower concentrations of formic acid tend to remove the smell and the pain associated with application of a wart mixture comprising formic acid. Earlier, it has been conventional wisdom that formic acid should be present in a high concentration, such as about 85%, to be effective against warts. The present invention appears to allow the treatment of warts using lower concentrations of formic acid. Lower concentrations allow more frequent, such as daily, application of the composition, and thus the concentration of active ingredients in situ may be kept approximately constant as compared to the situation where a composition is applied on a weekly basis. High concentration of formic acid is associated with the disadvantage of pain and creation of wounds upon accidental application on the skin surrounding a wart. Thus, high concentration of formic acid usually require longer intervals between application, as the skin needs time to reconstitute between treatments.

Further, no pretreatment with hot water or scraping of hard skin appeared necessary. In addition, as the smell was not repulsive as opposed to the Comparison Example, a composition of the present invention could readily be applied to the face, arms, legs and body of the patient with good compliance. A composition according to the invention could be applied to other parts of the skin, such as the hands and feet of the patients, with similar good compliance.

The invention claimed is:

1. A method of treating warts, comprising topically administering a composition to a patient in need thereof; wherein the composition comprises 80-85% (w/w) of formic acid, 15-20% (w/w) of at least one C1-C4 alkyl ester of lactic acid, and less than 5% (w/w) water, wherein the composition does not include a further active ingredient.

2. The method of claim 1, wherein said at least one C1-C4 alkyl ester is ethyl lactate.

3. The method of claim 1, wherein said composition is applied directly on the warts without puncturing the warts or scraping skin of the warts.

4. The method of claim 1, wherein said composition is applied on hard warts.

5. The method of claim 1, wherein said composition is applied on the palm or the foot sole.

6. The method of claim 1, wherein said composition is applied on soft warts.

7. The method of claim 1, wherein said composition is applied on other sites than the palm or the foot sole.

8. The method of claim 1, wherein said composition is applied on the back of the foot, the back of the hand, the face, neck, wrists, knees or genitalia.

9. The method of claim 1, wherein said composition comprises about 85% of formic acid (w/w); about 15% ethyl lactate (w/w); and substantially no water and/or alcohol.

10. The method of claim 1, wherein the composition comprises substantially no water.

11. The method of claim 1, wherein the composition comprises less than 3% water (w/w).

12. The method of claim 1, wherein the composition comprises at least 1% (w/w) and less than 5% (w/w) of water.

\* \* \* \* \*